(12) United States Patent
Pisharodi

(10) Patent No.: US 9,439,773 B2
(45) Date of Patent: *Sep. 13, 2016

(54) ENHANCED ARTIFICIAL DISK

(71) Applicant: Perumala Corporation, Brownsville, TX (US)

(72) Inventor: Madhavan Pisharodi, Brownsville, TX (US)

(73) Assignee: Perumala Corporation, Brownsville, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/947,023

(22) Filed: Nov. 20, 2015

(65) Prior Publication Data

US 2016/0067053 A1    Mar. 10, 2016

Related U.S. Application Data

(63) Continuation-in-part of application No. 14/272,043, filed on May 7, 2014, now Pat. No. 9,198,768.

(51) Int. Cl.
*A61F 2/44* (2006.01)
*A61F 2/30* (2006.01)

(52) U.S. Cl.
CPC ............... *A61F 2/442* (2013.01); *A61F 2/447* (2013.01); *A61F 2002/3098* (2013.01); *A61F 2002/30281* (2013.01); *A61F 2002/30431* (2013.01); *A61F 2002/30509* (2013.01); *A61F 2002/30515* (2013.01); *A61F 2002/30542* (2013.01); *A61F 2002/30553* (2013.01); *A61F 2002/30578* (2013.01); *A61F 2002/30596* (2013.01); *A61F 2002/4475* (2013.01); *A61F 2250/0004* (2013.01); *A61F 2310/00017* (2013.01); *A61F 2310/00023* (2013.01); *A61F 2310/00029* (2013.01); *A61F 2310/00161* (2013.01); *A61F 2310/00407* (2013.01); *A61F 2310/00413* (2013.01); *A61F 2310/00796* (2013.01)

(58) Field of Classification Search
CPC combination set(s) only.
See application file for complete search history.

(56) References Cited

U.S. PATENT DOCUMENTS

| | | |
|---|---|---|
| 3,716,050 A | 2/1973 | Johnston |
| 5,209,751 A | 5/1993 | Farris et al. |
| 5,549,679 A | 8/1996 | Kuslich |
| 6,106,557 A | 8/2000 | Robioneck et al. |
| 6,235,059 B1 | 5/2001 | Benezech et al. |
| 6,264,655 B1 | 7/2001 | Pisharodi |
| 7,534,268 B2 | 5/2009 | Hudgins et al. |
| 7,947,043 B2 | 5/2011 | Mutchler |
| 8,211,145 B2 | 7/2012 | Dalton |
| 8,216,312 B2 | 7/2012 | Gray |

(Continued)

OTHER PUBLICATIONS

USPTO NonFinal Office Action dated Aug. 20, 2014 for parent U.S. Appl. No. 14/272,043.

(Continued)

*Primary Examiner* — Jan Christopher Merene
(74) *Attorney, Agent, or Firm* — D'Ambrosio & Menon, PLLC; Usha Menon

(57) ABSTRACT

An enhanced artificial disk for stabilizing a pair of adjacent vertebrae. The enhanced artificial disk include a disk and a stabilizer. The stabilizer includes a substantially keyhole shaped opening for receiving a protrusion. By facilitating movement of the protrusion within the opening, the enhanced artificial disk is capable of exhibiting a normal range of motion associated with a healthy disk while limiting any abnormal range of motion.

13 Claims, 18 Drawing Sheets

(56) References Cited

U.S. PATENT DOCUMENTS

| | | |
|---|---|---|
| 8,317,843 B2 | 11/2012 | Pisharodi |
| 8,480,742 B2 | 7/2013 | Pisharodi |
| 2002/0058939 A1 | 5/2002 | Wagner et al. |
| 2003/0078583 A1 | 4/2003 | Biedermann et al. |
| 2004/0068319 A1 | 4/2004 | Cordaro |
| 2005/0277938 A1 | 12/2005 | Parsons |
| 2006/0235533 A1* | 10/2006 | Blain ............. A61B 17/7059 623/17.16 |
| 2006/0282165 A1 | 12/2006 | Pisharodi |
| 2007/0032873 A1 | 2/2007 | Pisharodi |
| 2007/0043441 A1 | 2/2007 | Pisharodi |
| 2007/0088439 A1 | 4/2007 | Thramann |
| 2007/0123989 A1 | 5/2007 | Gfeller et al. |
| 2007/0233107 A1 | 10/2007 | Zielinski |
| 2008/0249572 A1 | 10/2008 | Tandon |
| 2008/0300634 A1 | 12/2008 | Gray |
| 2009/0182430 A1 | 7/2009 | Tyber et al. |

OTHER PUBLICATIONS

USPTO Final Office Action dated Dec. 3, 2014 for parent U.S. Appl. No. 14/272,043.

USPTO NonFinal Office Action dated Mar. 18, 2015 for parent U.S. Appl. No. 14/272,043.

* cited by examiner

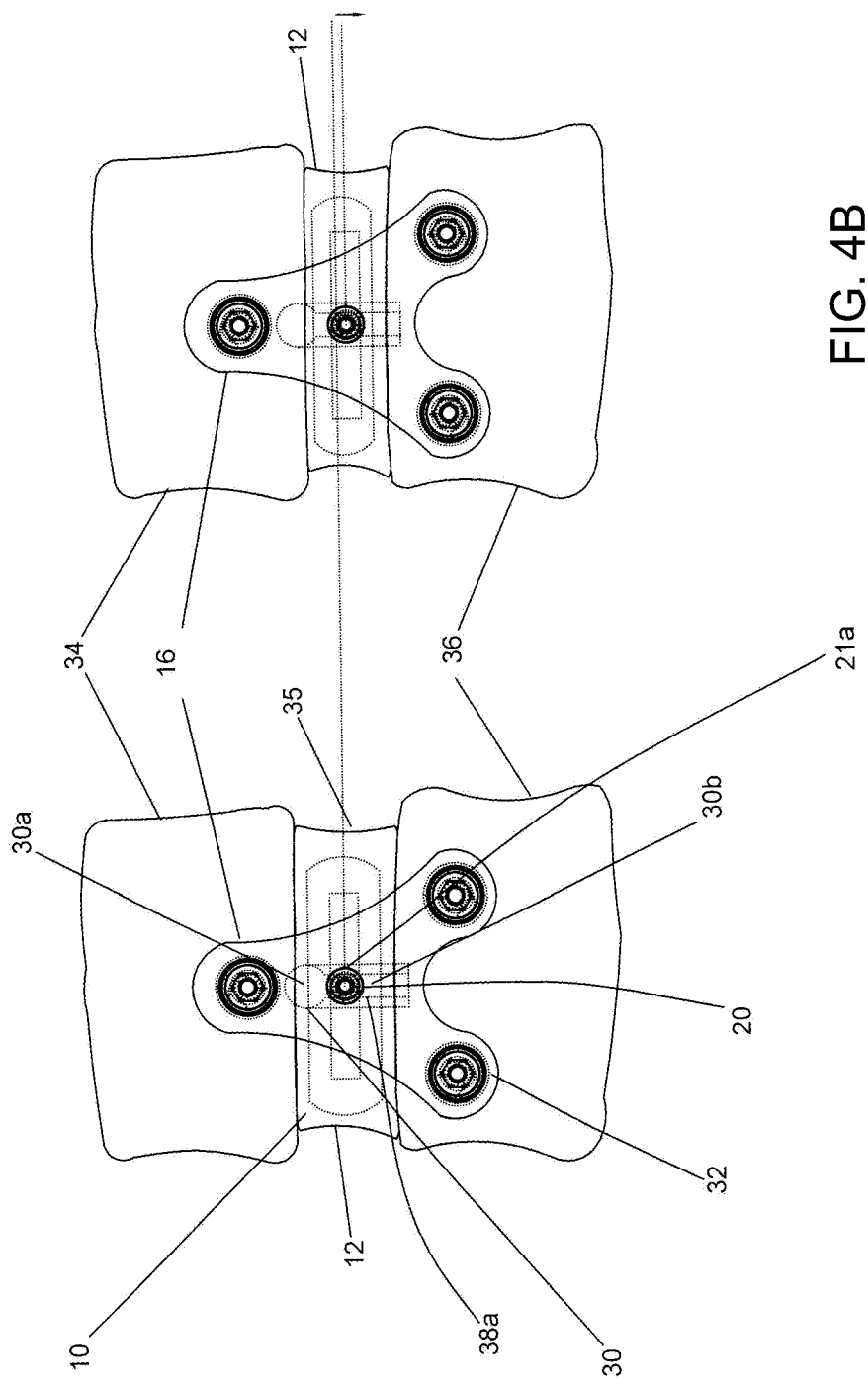

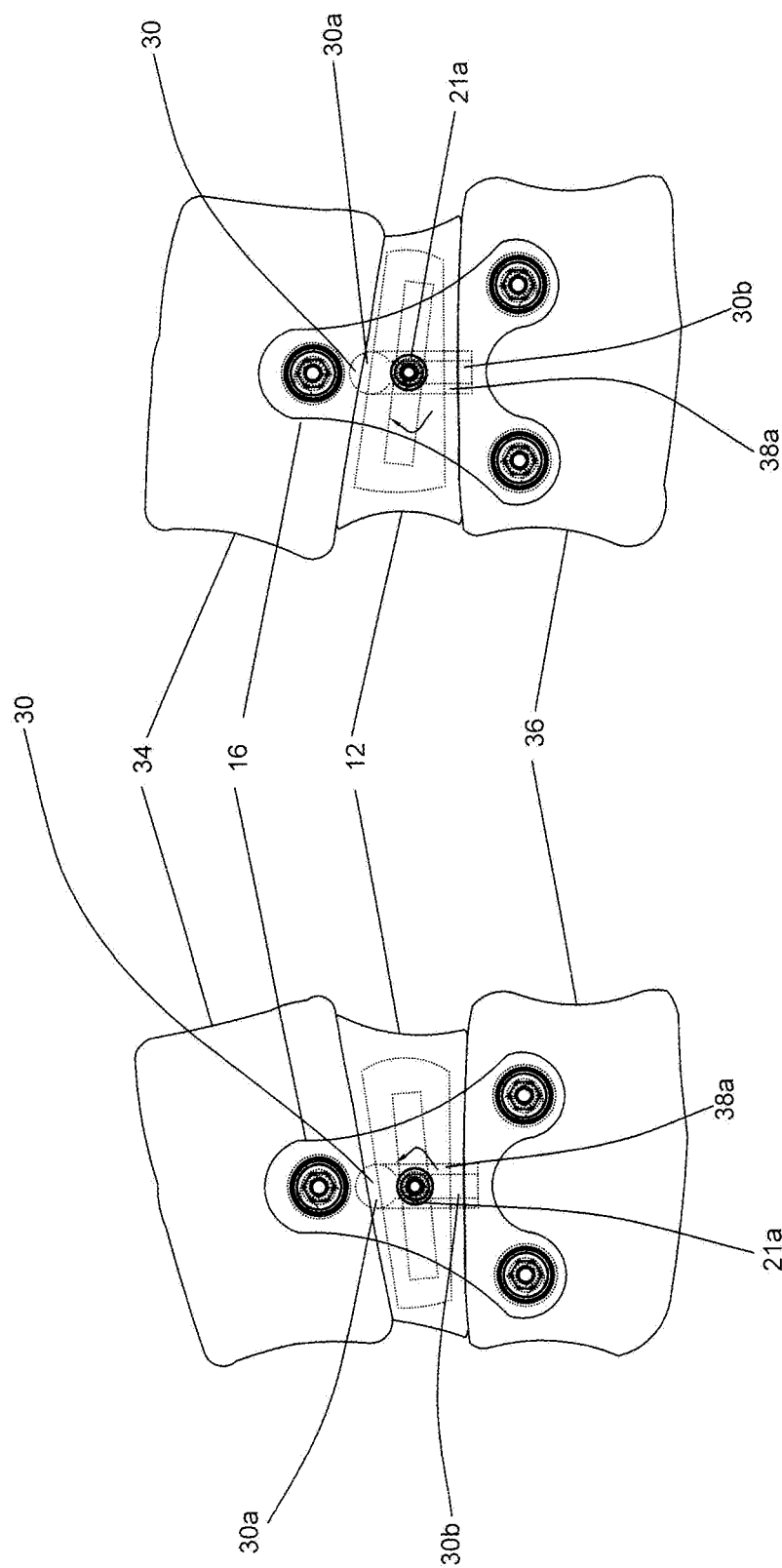

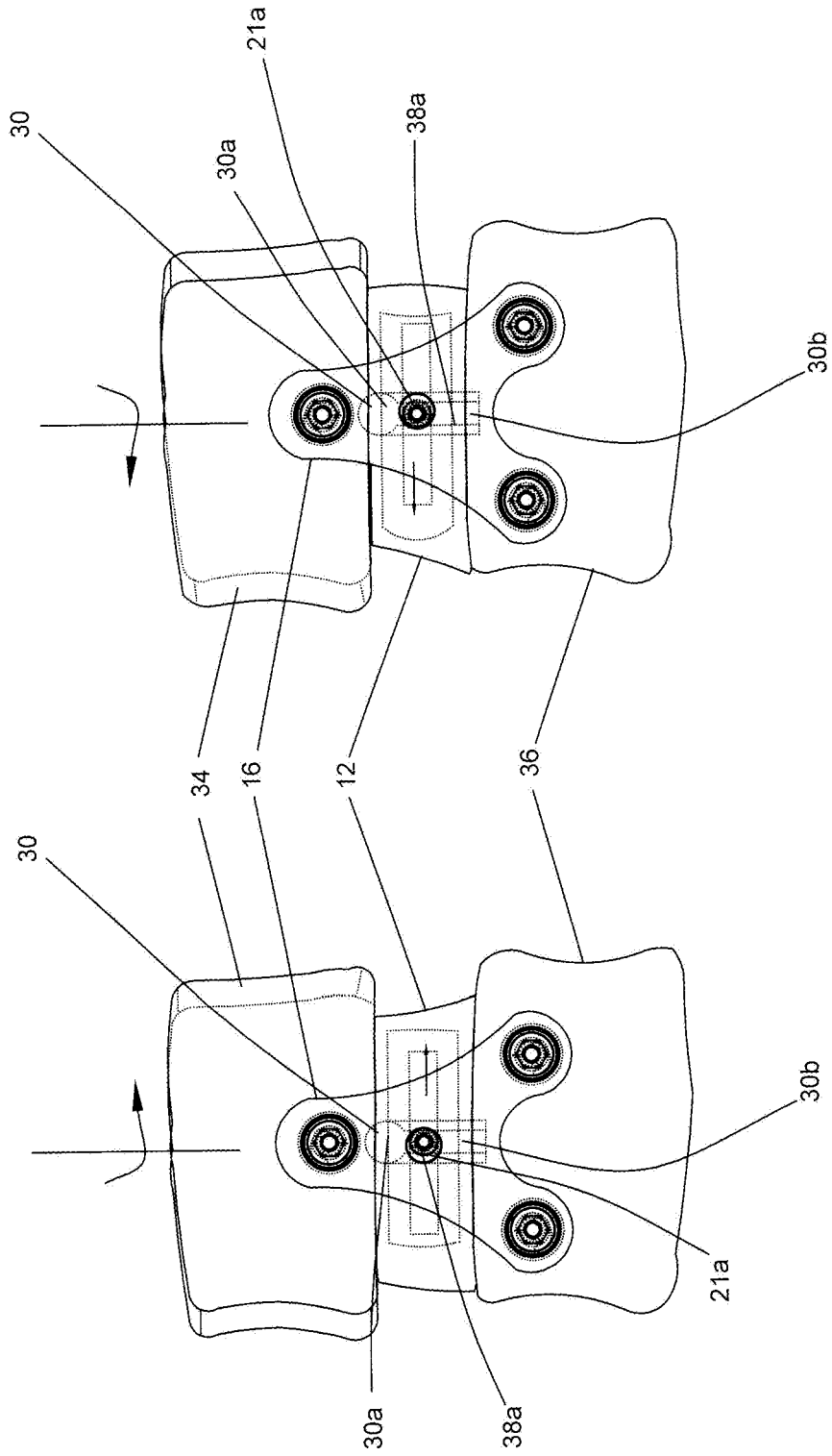

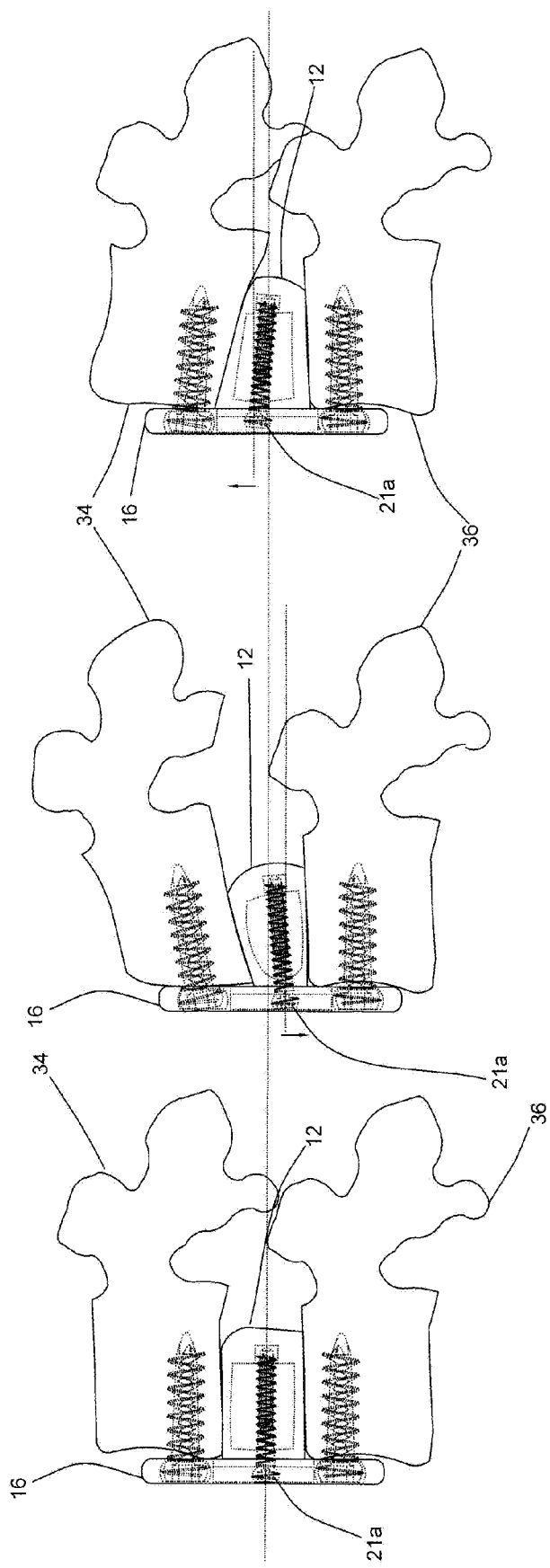

ENHANCED ARTIFICIAL DISK

PRIORITY CLAIM

This application is a continuation-in-part of and claims priority to U.S. Ser. No. 14/272,043 filed May 7, 2014, which issued as U.S. Pat. No. 9,198,768, the contents of which are incorporated by reference herein. This application also claims priority Indian application no. 213/KOL/2015 filed Feb. 26, 2015, the contents of which are incorporated by reference herein.

BACKGROUND AND FIELD OF THE INVENTION

The present invention relates to an enhanced artificial disk and a method of stabilizing two adjacent vertebrae. More specifically, the present invention relates to an artificial disk and stabilizer which when used retains the properties of cushioning while resisting any abnormal mobility of the spine, as well as allowing normal range of motions, that characterize the healthy, normal intervertebral disk.

SUMMARY OF THE INVENTION

The injured, deformed, diseased, and/or degenerated human spine is a source of great pain in many patients, and there are many approaches to management, treatment, and/or prevention of that pain, including surgical intervention. One particularly vexing source of spinal pain and/or dysfunction is the damaged intervertebral disk. Healthy intervertebral disks are a necessity to pain-free, normal spinal function, yet disk function is all too frequently impaired by, for instance, disease or injury.

The anatomy of the intervertebral disk correlates with the biomechanical function of the disk. The three major components of the disk that are responsible for the function of the disk are the nucleus pulposus, annulus fibrosus, and cartilagenous endplate. The nucleus pulposus is the centrally located, gelatinous network of fibrous strands, surrounded by a mucoprotein gel, that prevents buckling of the annulus and maintains the height of the disk (and therefore, provides the cushioning effects that are so important to complement other functions of the disk) through osmotic pressure differentials. The water content of the disk changes in accordance with the load on the spine, water being driven out of the pulposus under heavy load. The annulus fibrosus encapsulates the disk, resisting both tension and compression loads and bearing axial loads. The vertebral endplates are cartilagenous in nature and "sandwich" the other components of the disk, distributing load over the entire disk and providing stability during normal spinal movements. The three elements work in cooperative fashion to facilitate disk function, and impairment of any of the elements compromises the functions of the other elements.

The two main surgical treatments of the intervertebral disk substitution include total disk and nuclear replacement, but unfortunately, both treatments represent a number of compromises that simply do not provide normal disk function. The total artificial disk prosthesis is a total prosthetic replacement of the annulus fibrosus and nucleus pulposus with an endplate that interfaces with the patient's own vertebral endplates. Prothetic replacement devices typically include metallic ball and socket joint type devices. These devices are incapable of approximating the functionality of a normal disk. On the contrary, these devices cause excessive movement and can result in facet joint arthropathy. Also, capturing and securing the total disk prosthesis to the host vertebral endplates can be a challenge because of the asymmetrical and cyclic loads placed upon the spine that can place excessive stresses on both the host bone and the interface between the prosthesis and the endplates, resulting in early loss of fixation and may potentially lead to vertebral fracture. Many presently available total disk prostheses are designed to mimic the function of normal joints, but in that aspect, they are non-physiological in the sense that the normal spine does not have actual joints or sliding functions, but does have an inherent shock absorbing function. This lack of cushioning and shock absorbing function may be the contributing factor for the settling of the prosthesis into the vertebral body.

Nuclear replacement is intended to replace a damaged nucleus pulposus with a device that is intended to restore disk height while maintaining the kinematics of the gel that comprises the healthy, intact nucleus pulposus. Although less invasive of the spine, implant extrusion and migration of the implant are all too frequent complications of nuclear replacement surgery.

The problem of maintaining the spacing between vertebrae is particularly acute in the cervical vertebrae. The surgery itself is not as difficult as in the lumbar spine because access to the intervertebral space is from the front in the cervical spine, e.g., ventrally to the patient. Bone chips are not substantial enough to maintain the spacing between vertebrae, so the accepted surgical method to maintain spacing between adjacent vertebrae in the cervical spine is to scoop out the entire damaged disk, clean out the intervertebral space, and insert a plug of the patient's bone, a cage, a spacer or an artificial disk into the space between vertebrae.

Treatment of a herniated disk in the neck and in the lumbar region continues to be a challenging field of medicine. There is, therefore, a need for a device that is intended to overcome the disadvantages and limitations of these prior art devices. The new device should be able to resist abnormal movement of one vertebra relative to an adjacent vertebra while allowing a normal range of motion. The new device should also be able to provide a cushioning function that approximates the normal function of the intervertebral disk under compression load. The new device should also have an axis of movement that approximates normal disk motion.

In an embodiment of the invention, an enhanced artificial disk is proposed. The enhanced artificial disk may include an artificial intervertebral disk (called "disk" hereinafter) and a stabilization means (called "stabilizer" hereinafter) of the disk that does not interfere with the function of the disk. The stabilizer can function as a restraining device to hold the disk in position. Conveniently, the stabilizer is not intended to function as a weight or load bearing device. In a pre-assembled configuration, the stabilizer is pre-mounted to the disk to facilitate ease of insertion of the enhanced artificial disk in an intervertebral disk space.

The enhanced artificial disk can provide cushioning and shock absorption function that approximates a normal disk under compression load. The enhanced artificial disk also facilitates the maintenance of an optimal disk height when it is inserted within an intervertebral disk space. The enhanced artificial disk can substantially improve the functional activities of the patient. The enhanced artificial disk can approximate the range of motion of a normal spine. For example, the enhanced artificial disk may be capable of flexion, extension, compression, left and right lateral flexion and also left and right rotation. The enhanced artificial disk can also prevent any abnormal movement of the disk thereby reducing any stress on facet joints. Furthermore, the enhanced artificial disk can enable an adjustment of intradiskal pressure to a desired level.

These and other advantages of the present invention, will be made clear to those skilled in the art in the following detailed description of the embodiments of the present invention and the drawings appended hereto. Those skilled in the art will recognize, however, that the embodiments of the invention described herein are only examples provided for the purpose of describing the making and using of the present invention and that they are not the only embodiments of artificial disks that are constructed in accordance with the teachings of the present invention.

BRIEF DESCRIPTION OF THE DRAWINGS

The features and advantages of certain embodiments will be more readily appreciated when considered in conjunction with the accompanying figures. The figures are not to be construed as limiting any of the preferred embodiments.

FIGS. 4A-4F are front elevational views showing normal, compression, right flexion, left flexion, left rotation and right rotation respectively of an enhanced artificial disk in the intervertebral space in accordance with an embodiment of the invention.

FIG. 4I depicts a neutral side view the enhanced artificial disk in the intervertebral space in accordance with an embodiment of the invention.

FIGS. 4J and 4K depict side views showing flexion and extension respectively of an enhanced artificial disk in the intervertebral space in accordance with an embodiment of the invention.

DETAILED DESCRIPTION OF THE INVENTION

Figure 1A:
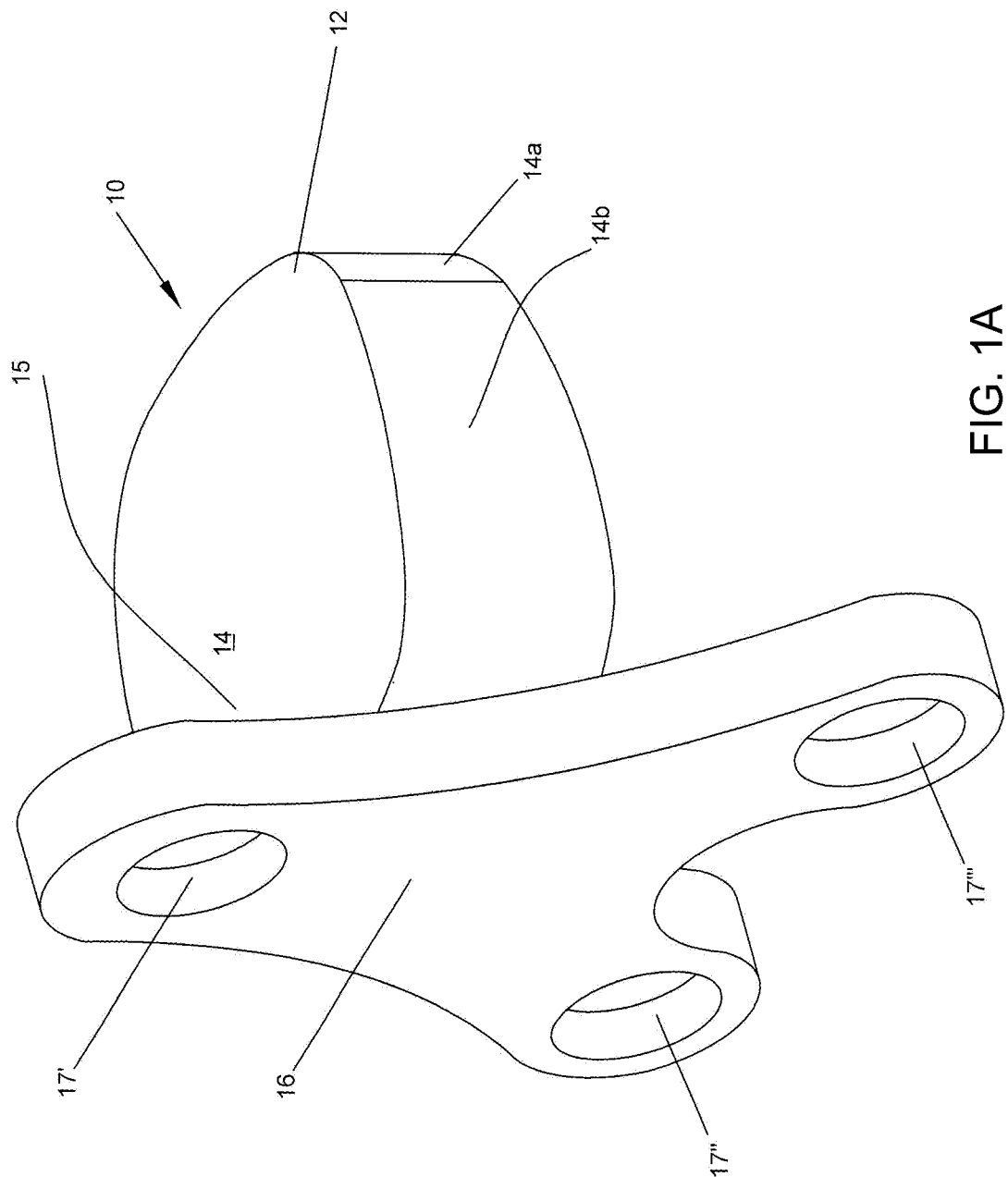
FIG. 1A is a perspective view of a pre-assembled enhanced artificial disk in accordance with one embodiment of the invention.

FIG. 1A depicts a pre-assembled enhanced artificial disk 10 in accordance with an embodiment of the invention. As used herein, the term "enhanced" artificial disk is intended to include an artificial disk that is capable of approximating the range of motion of a normal disk while providing the cushioning effect of a normal disk. The enhanced artificial disk is also capable of adjusting the desired intradiskal pressure inside the disk.

Also, as used herein, the words "comprise," "have," "include," and all grammatical variations thereof are each intended to have an open, non-limiting meaning that does not exclude additional elements or steps.

The enhanced artificial disk 10 may include a disk 12 and a stabilizer 16. The stabilizer 16 can be mounted to a first end 15 of the disk 12. The stabilizer 16 can include a plurality of holes 17', 17", 17"'. The disk 12 may include a cushion 14. An exemplary disk has been described in U.S. Pat. No. 8,480,742, the contents of which are incorporated in their entirety.

The cushion 14 may comprise a resilient, polymeric material. The cushion may further comprise a substantially firmer outer region 14a and a substantially softer inner region 14b. The same material, but with differing consistencies, may be used in manufacturing both outer region 14a and inner region 14b. For example, the outer region 14a could be relatively denser in consistency to approximate the consistency or density of the annulus fibrosis of a normal disk. The inner region 14b can be relatively less dense to approximate the consistency or density of the nucleus pulposis of a normal disk. In another embodiment, the substantially firmer outer region 14a and the substantially softer inner region 14b may be made out of different materials. Although not limited to these materials, the cushion 14 may be molded from a biocompatible, viscoelastic polymer such as silicone, a urethane such as a polycarbonate urethane, or a polyurethane. The cushion 14 may also be molded from synthetic silk-elastin copolymers, polymethyl- or polyethylmethacrylate, polyethylene or polyacrylonitrile that absorbs water and increases in volume upon absorption of water, thereby functioning to maintain disk height in a manner similar to the manner in which the healthy disk maintains proper spacing between adjacent vertebrae.

The cushion 14 may also be made of a suitable compressible material that can be made to approximate the range of compressibility of a natural or normal disk. The compressibility can be adjusted from a spectrum ranging from minimally compressible to maximum compressibility to anywhere in between depending on the patient to be treated. For example, the cushion 14 can be adjusted to be minimally compressible, that is, relatively firm, when the patient to be treated does not present symptoms of osteoporosis (that is, the vertebrae are normal). The cushion 14 can be adjusted to be maximally compressible, that is, relatively soft, when the patient to be treated has osteoporosis so that the disk 12 does not telescope into an adjoining bone.

Figure 2A:
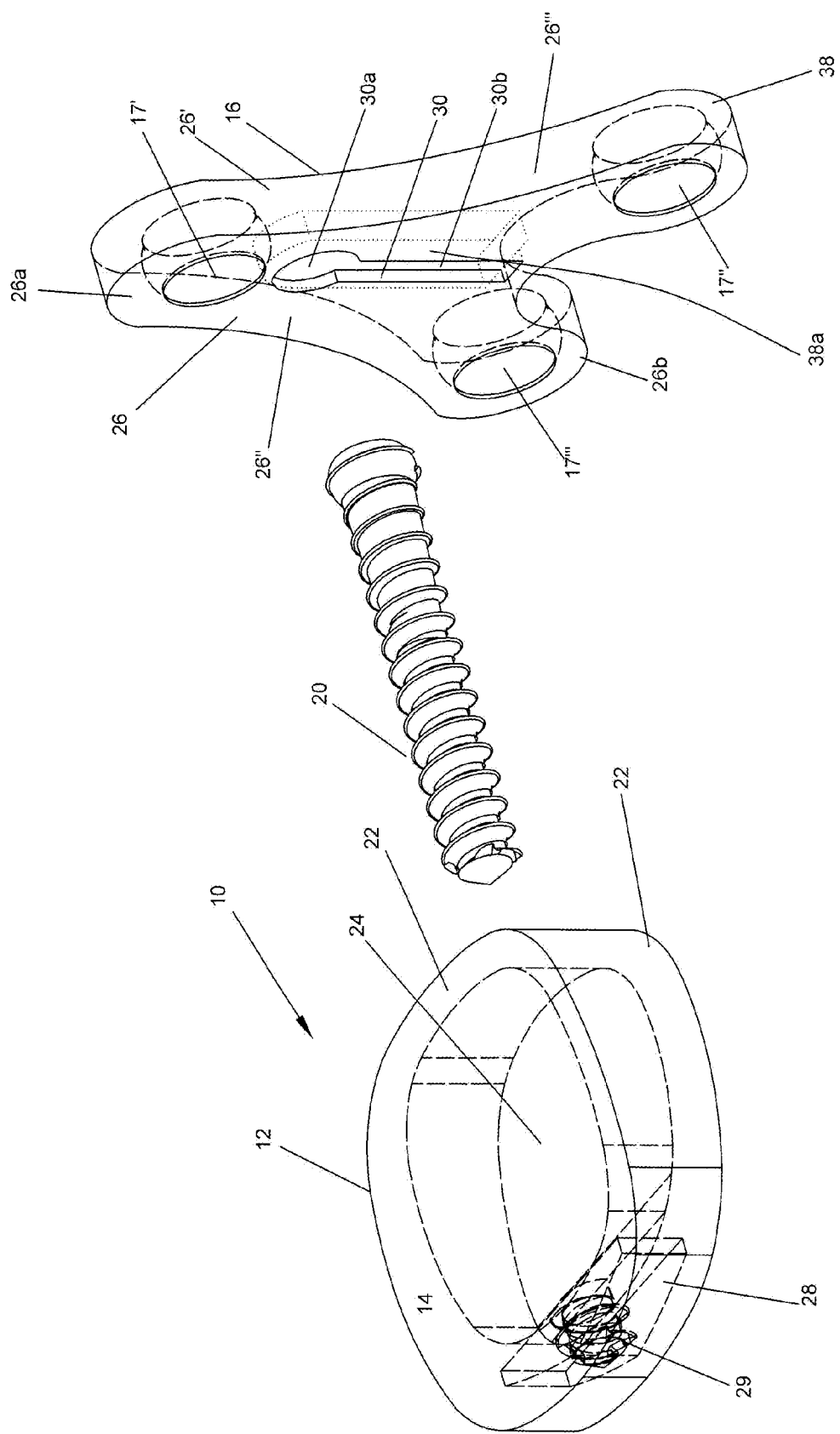
FIG. 2A is an exploded view of the various components of a pre-assembled enhanced artificial disk in accordance with an embodiment of the invention.

As shown more clearly in FIG. 2A, the cushion 14 may be molded in a shape that approximates the shape of a normal disk. The top and bottom surfaces 22 of the cushion 14 may be arched. The top and bottom surfaces 22 of the cushion 14 may be provided with a textured or grooved surface to facilitate the ingrowth of bone onto the surfaces 22.

Figure 1B:
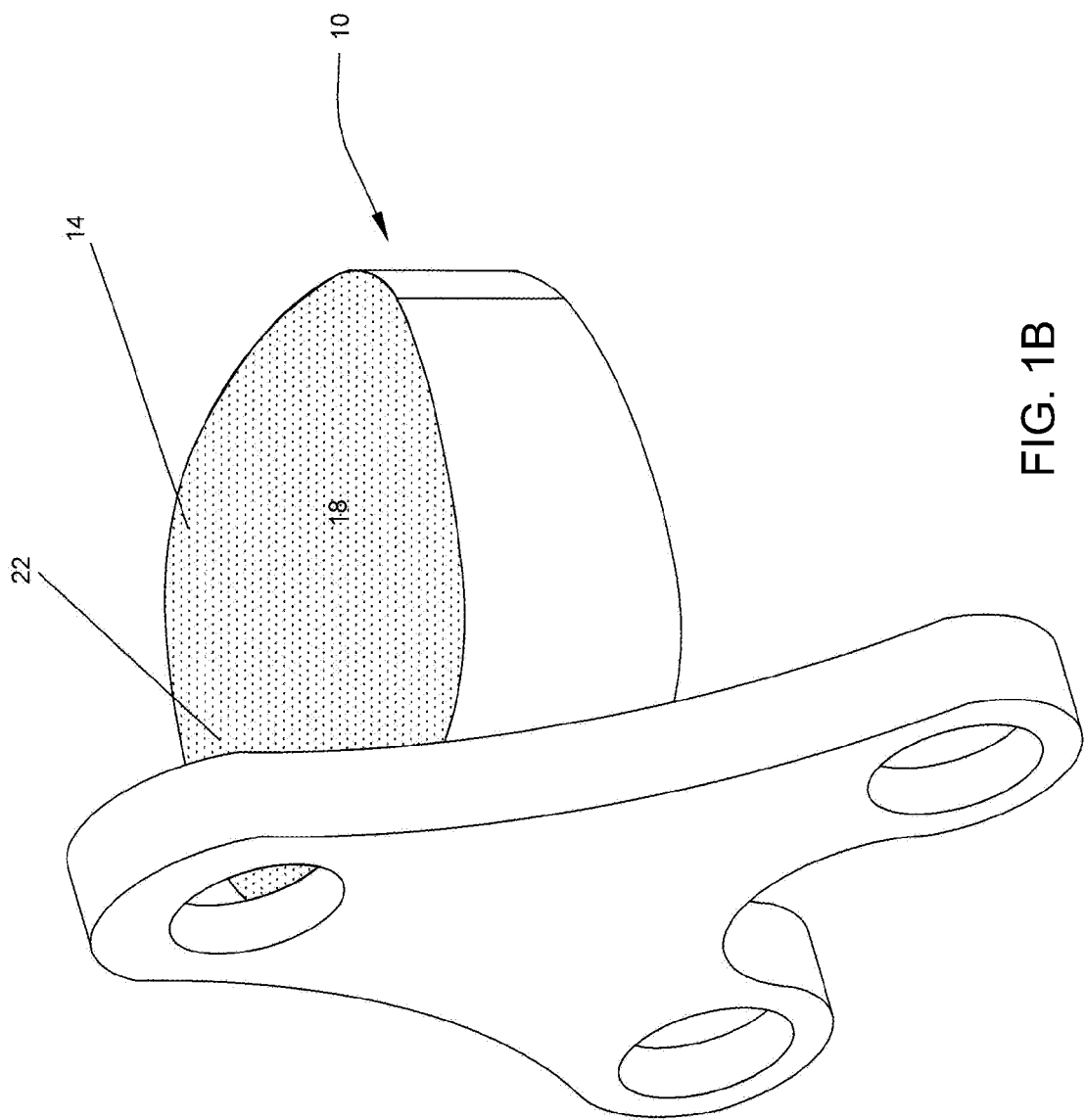
FIG. 1B is a perspective view of a pre-assembled enhanced artificial disk having a coated disk in accordance with another embodiment of the invention.

As shown in FIG. 1B, one or both of the surfaces 22 of the cushion 14 of the enhanced artificial disk 10 may be covered with a coating 18. For example, the coating 18 may include a porous or roughened titanium coating or a layer of calcium phosphate for this purpose; other suitable coatings/surfaces are known in the art and include titanium wire mesh, plasma-sprayed titanium, porous cobalt-chromium and bioactive materials such as hydroxyapatite and the aforementioned calcium phosphate.

Figure 2B:
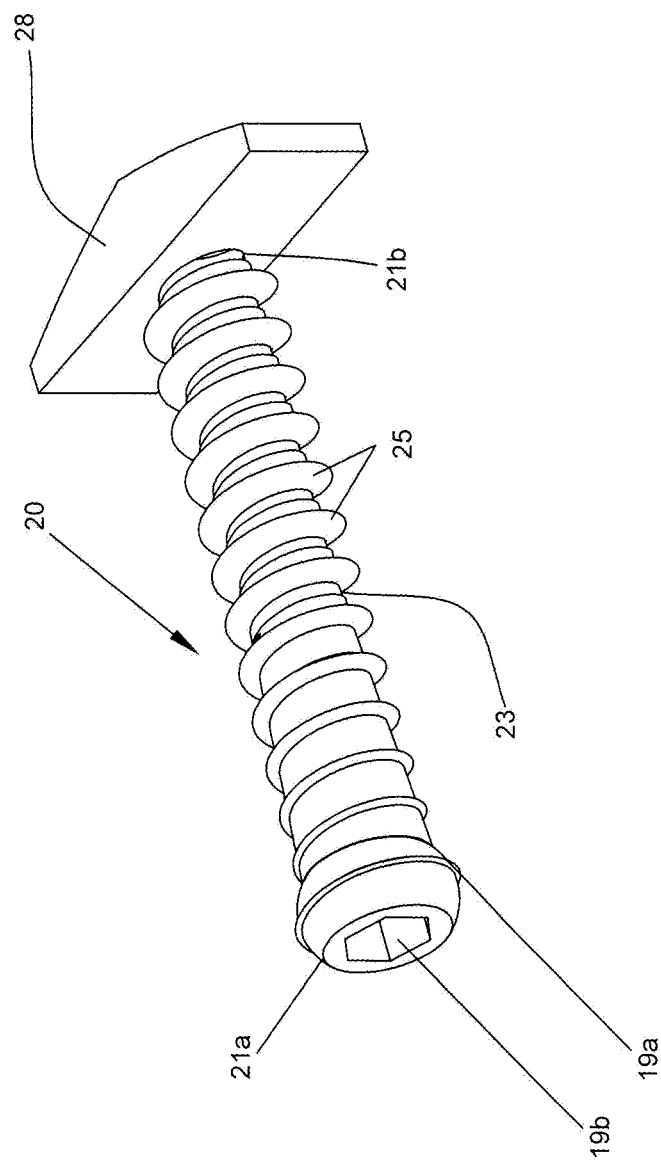
FIG. 2B is a perspective view of a stabilizer screw in accordance with an embodiment of the invention.
Figure 2C:
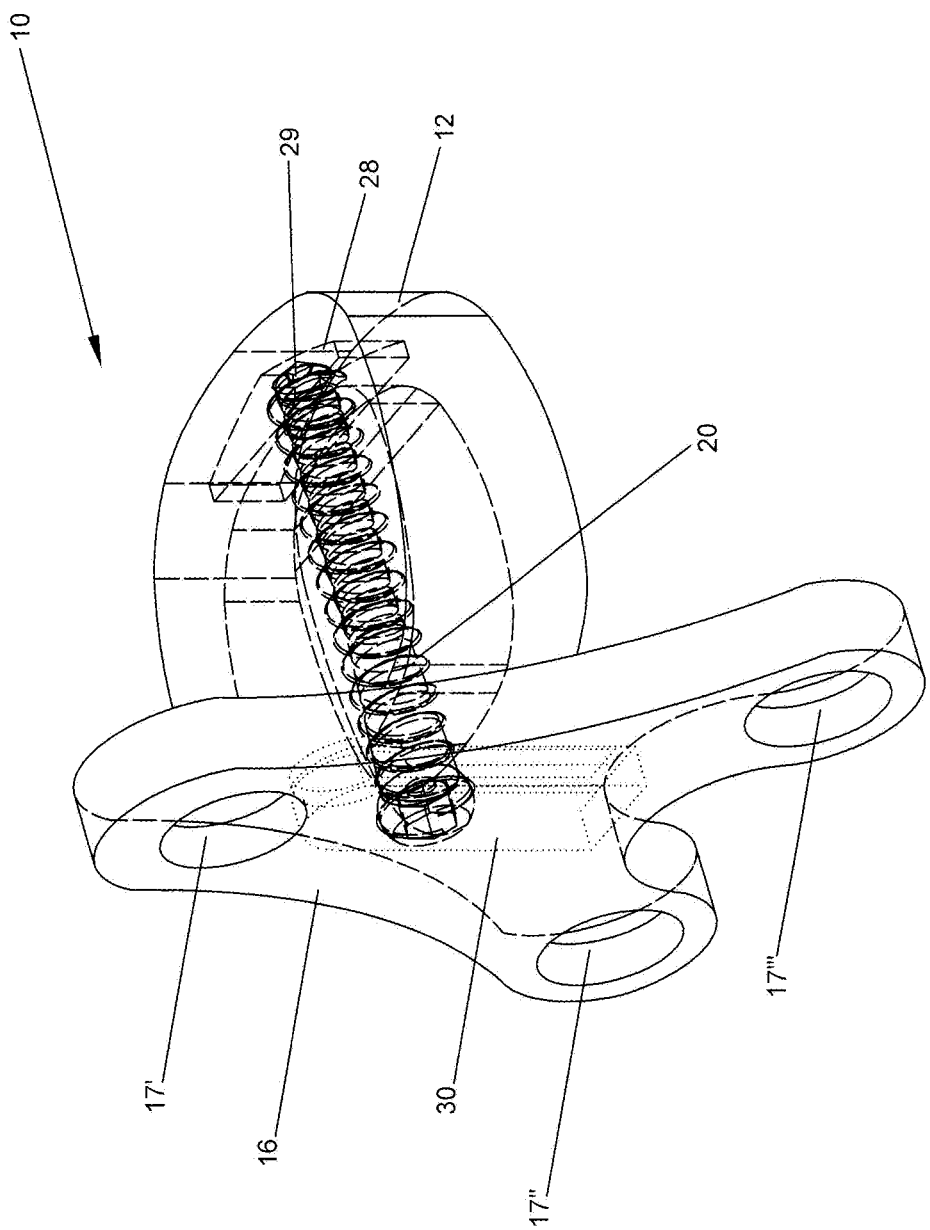
FIG. 2C is a perspective view of a pre-assembled enhanced artificial disk in accordance with an embodiment of the invention.

FIG. 2A depicts an exploded view of the various components of the preassembled enhanced artificial disk 10 while FIG. 2C depicts another perspective view of the pre-assembled artificial disk 10. As shown in both FIG. 2A and FIG. 2C, the components may include a disk 12, stabilizer 16 and a stabilizer screw 20.

Referring to FIG. 2A, the cushion 14 may be provided with a central hollow space 24. The hollow space 24 may be shaped to approximate the shape of the nucleus pulposus, however, those skilled in the art who have the benefit of this disclosure will recognize that the hollow space 24 need not be shaped in this shape and that, depending upon the particular pathology that necessitates the disk replacement, it may even be advantageous to shape the hollow space 24 differently in contemplation of varying kinematic characteristics. The stabilizer 16 may include an enclosure or casing 38. The casing 38 may comprise a substantially triangular-shaped outer or front wall 26' and a substantially triangular-shaped inner or rear wall 26". The front wall 26' and rear wall 26" may be connected by a bridge 26'". As shown, the bridge 26'" may be substantially arched in the middle. The rear wall 26" may also include an opening 30 described below. The opening 30 may lead into a substantially elongate hollow cavity 38a. The cavity 38a may be formed between front wall 26' and rear wall 26"

Figure 5:
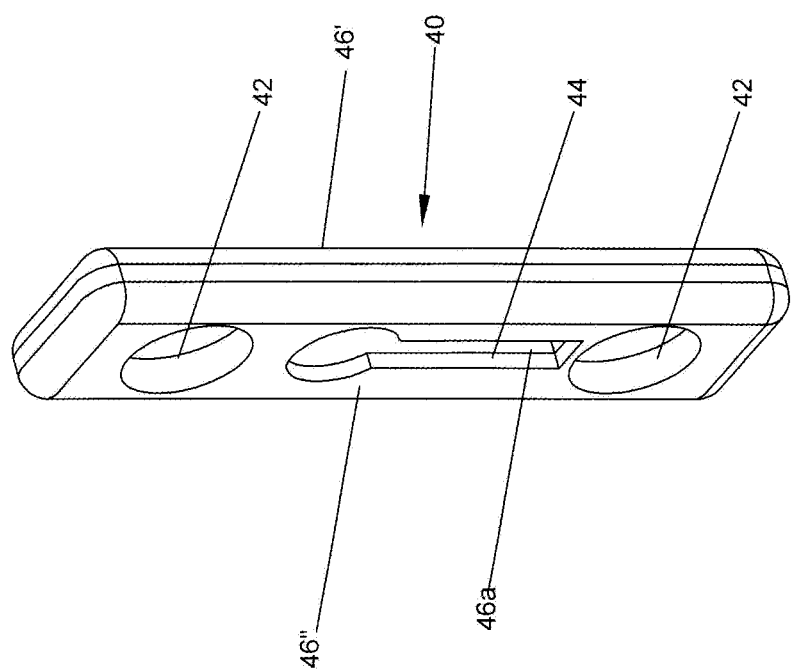
FIG. 5 is a perspective view of a stabilizer in accordance with another embodiment of the invention.

The base of the stabilizer 26b may be substantially U-Shaped. It should be understood, however, that the stabilizer 16 may be configured and dimensioned in any manner that can provide optimal stability to the disk 12. For example, another embodiment of a stabilizer 40 is depicted in FIG. 5. As shown in FIG. 5, the stabilizer 40 may include a frame 46 that may be substantially elongate. The frame 46 may include a substantially rectangular front wall 46' and a substantially rectangular rear wall 46", at least a pair of through-holes 42 and an opening 44. A hollow cavity 46a may be formed within the frame 46.

As shown in FIG. 2B, stabilizer screw 20 may be comprised of a globular or hemispherical head 21a and an elongate shank 23 with threads 25 along the length of the shank 23. The term "screw" as used herein is meant to encompass any fastener or attachment means that is capable of piercing a material, for example, a disk, and secureably coupling the stabilizer with the disk. The head 21a may be provided with a screw thread 19a on the surface thereof. The screw thread 19a may extend only approximately a single turn around the circumference of head 21. A socket 19b opens to the top of the head 21a of stabilizer screw 20. In another embodiment (not shown), the screw head 21a may be devoid of a socket.

FIG. 2C represents a schematic view of an embodiment of the preassembled enhanced artificial disk 10. Referring to FIGS. 2A and 2C, the front and rear walls 26', 26" of stabilizer 16 may have a number of through-holes 17', 17", 17'" formed therein. The through-holes 17', 17", 17'" are designed to go through the front wall 26' to the rear wall 26".

The front and rear walls 26', 26" may have at least three through-holes 17', 17", 17'". The through-holes 17', 17", 17'" may be formed near the periphery of the stabilizer 16. For example, a first through-hole 17' may be formed substantially near an upper end of the stabilizer 26a and a second and a third through-hole 17", 17'" may be formed substantially near the base of the stabilizer 26b.

Figure 3A:
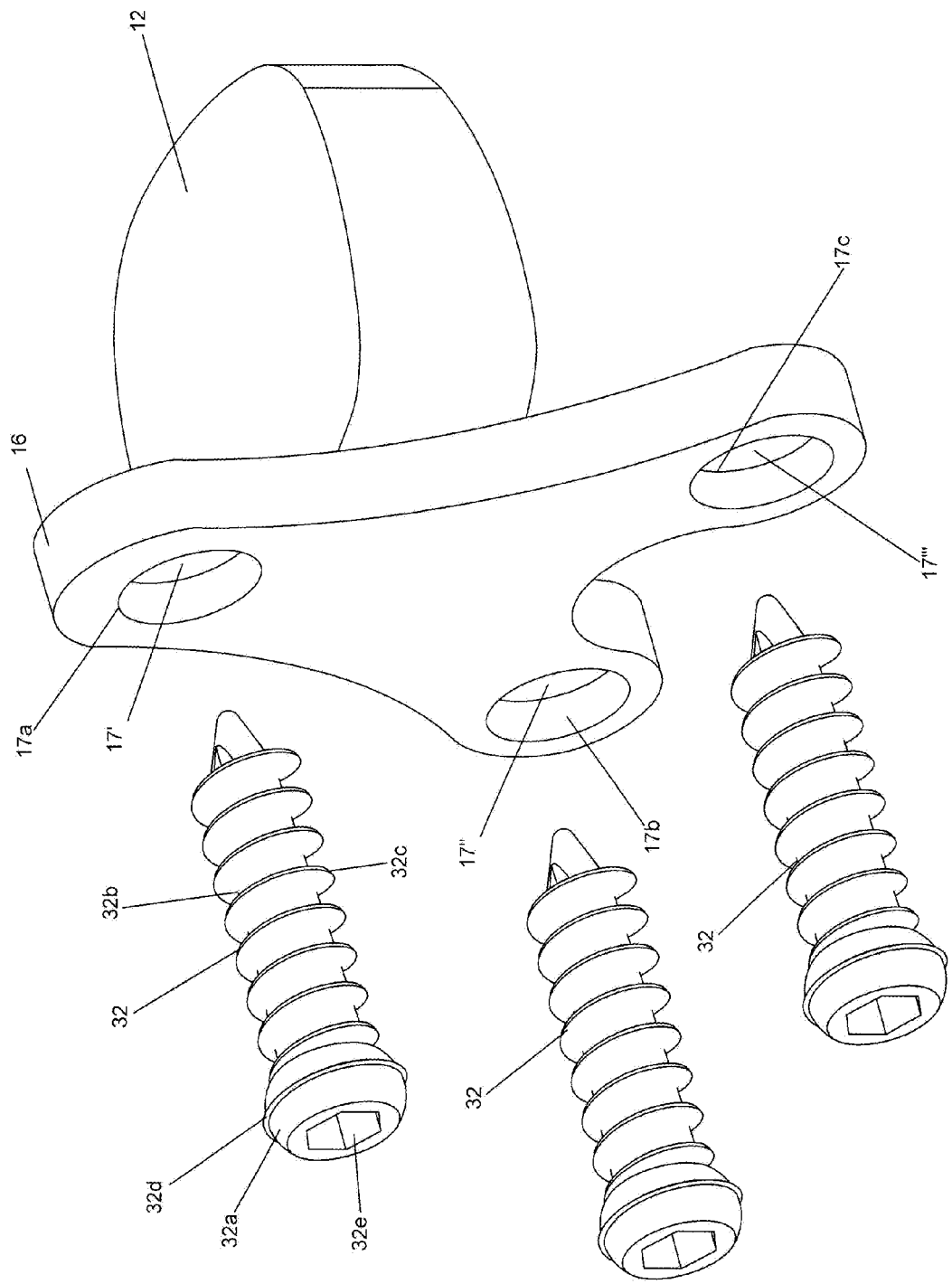
FIG. 3A is an exploded view of the components of a pre-assembled enhanced artificial disk in accordance with an embodiment of the invention.

As shown in FIG. 3A, one or more nails 32 may be received within through-holes 17', 17", 17'" formed within stabilizer 16 and such that the disk 12 is held secureably in place when it is inserted in the intervertebral disk space when the nails 32 are driven into a pair of vertebral bodies above and below (as described later). The term "nails," as used herein, includes bolts, screws and any other anchoring or fastening means. Each nail 32 may include an elongate shank 32b for screwing the nail 32 into the vertebral bodies above and below. The shank 32b may include one or more threads 32c. The diameter of the head 32a of the nail 32 may be slightly larger than the diameter of through-holes 17', 17", 17'". The head 32a may include a single thread 32d that extends approximately a single turn around the circumference of the head 32a. The thread 32d on the head 32a is included in the calculation of the diameter of the head 32a. The head 32a may include a hexagonal socket 32e for receiving an Allen wrench, or hex key (not shown), of corresponding size. The socket 32e may terminate in a left-hand threaded bore (not shown) in its deep end, the axis of which may be coincident with the axis of socket 32e in order to facilitate the removal of the nails 32 The through-holes 17', 17", 17'" are designed for the nails 32 to go through the front wall 26' to the rear wall 26" and into a pair of adjacent vertebrae above and below.

Figure 3B:
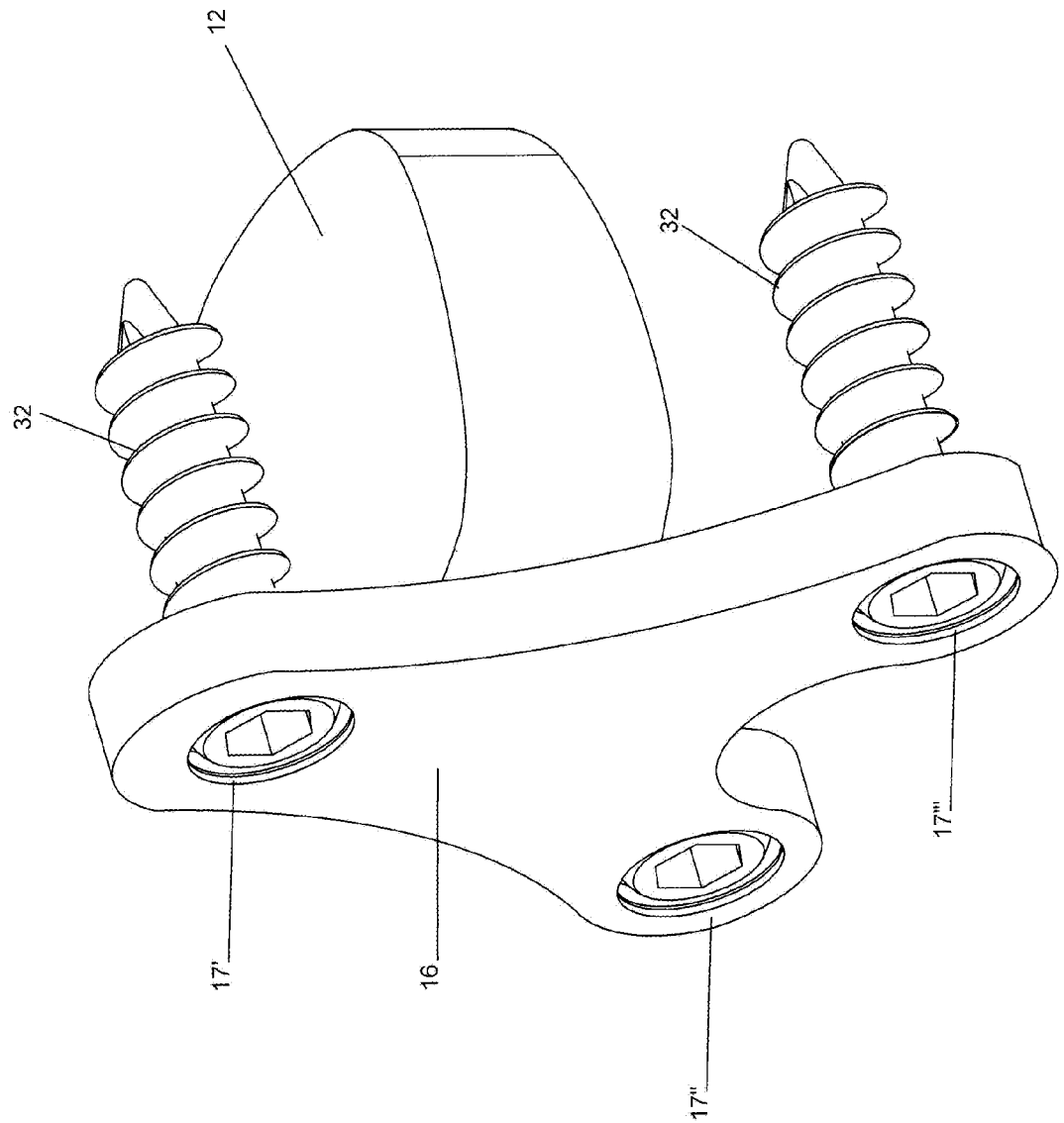
FIG. 3B is a perspective view of an assembled enhanced artificial disk in accordance with an embodiment of the invention.

Referring now to FIGS. 3A and 3B, the interaction between the head 32a of nail 32 and through-holes 17', 17", 17'" in stabilizer 16 is shown in more detail. FIG. 3B shows an assembled view with the disk 12 held in position by the stabilizer 16 and the nails 32. The nails 32 are driven into a pair of vertebral bodies (as described later). Each of the through-holes 17', 17", 17'" in stabilizer 16 is comprised of an outer aperture 17a, a central concave portion 17b and an inner opening 17c on one side of stabilizer 16 (referred to herein as the top of stabilizer 16, but those skilled in the art that the word "top" is a relative term intended to denote direction and/or orient the user of stabilizer of the present invention rather than to delimit or restrict the stabilizer to a particular configuration or structure), an opening 17" at the bottom left of stabilizer 16 and an opening 17" at the bottom right of the stabilizer 16 (the term "bottom left" and "bottom right" likewise being intended for the purpose or orienting the user rather than to require certain structure). The walls, or margins, of the central portion 17b of through-holes 17', 17", 17'" are concave so that the generally rounded, or hemispherically-shaped, head 32a of nail 32 resides in the rounded central portion 17b of through-holes 17', 17", 17'" when the head 32a of nails 32 is rotated through the through-holes 17', 17", 17" of the stabilizer 16 as described below. The inner opening 17c of through-holes 17', 17", 17" is narrower than the outer opening 17a of the through-holes 17', 17", 17" such that the head 32a of the nails 32 cannot escape from the through-holes 17', 17", 17'" into the vertebral bodies.

The diameter of the head 32a of nails 32 is slightly larger than the diameter of the apertures 17a of the through-holes 17', 17", 17'" (note that the thread 32d on head 32 is being included in the diameter of the head 32a of nails 17) and, in a preferred embodiment, the stabilizer 16 is comprised of a material that is capable of being cut through, or scored by, the material comprising nails 32 so that when the nails 32 are inserted into through-holes 17', 17", 17''' and rotated relative to stabilizer 16, the head 32a of the nails 32 is pulled through apertures 17a on the thread 32d so that the head 32a resides in the central portion 17b of through-holes 17', 17", 17'''. Those skilled in the art will recognize that stabilizer 16 may be comprised of a physiologically inert polymer, titanium, stainless steel, or other suitable material and that nails 32 may be comprised of a physiologically inert ceramic, polymer, metal, or metal alloy that is harder than the material comprising stabilizer 16 so that the thread 32d on the head 32a of nail 32 "bites into" or cuts through the material comprising stabilizer 16 for this purpose. Alternately, both nails 32 and the stabilizer 16 may be of same material and the head of the nails 32 can be made to advance by the application of external pressure. Once the head 32a is positioned in the central portion 17b of through-holes 17', 17", 17''', however, the thread 32d may no longer engage the margin of through-holes 17', 17", 17''' and may therefore be free to rotate and/or pivot relative to stabilizer 16 while being retained in the central inner portion 17b of through-holes 17', 17", 17''' by the smaller outer diameter of apertures 17a of through-holes 17', 17", 17'''. As mentioned earlier, the inner opening of through-holes 17c is narrower than the outer opening 17a of the through-holes 17', 17", 17'''.

As shown in FIGS. 2A and 2B, the tip 21b of stabilizer screw 20 may be dimensioned to fit tightly within a groove 29 of anchor 28. The anchor 28 may be wedge-shaped. The anchor 28 may be positioned inside the disk 12.

Referring now to FIGS. 2A and 2C, the rear wall 26" of the stabilizer 16 may include an opening 30. The opening 30 may be substantially keyhole shaped. For example, the opening 30 may include a substantially rounded crown 30a and an elongate slit-shaped tail 30b extending from a lower end of the crown 30a. The crown 30a may be dimensioned to receive the head 21a of stabilizer screw 20. In a pre-assembled configuration, the head 21a of the stabilizer screw 20 may be positioned inside the opening 30 and the tip 21b of the stabilizer screw 20 may be secureably positioned inside a groove 29 formed in anchor 28 positioned within the disk 12.

The hemispherically-shaped head 21a of the stabilizer screw 20 can reside in the rounded crown 30a of the opening 30 when the head 21a of the stabilizer screw 20 is rotated through the crown 30a in the opening 30. Once the head 21a of stabilizer screw 20 is inserted in the crown 30a of opening 30, the head 21a can rotate or move around inside the cavity 38a in the stabilizer 16. The diameter of the bulbous head 21a of the stabilizer screw 20 may be slightly larger than the width of the elongated slit 30b and bulbous head 21a may be slightly smaller than the width of the cavity 38a so that the stabilizer screw 20 can migrate downward from the crown 30a to the bottom of the elongated slit 30b by moving within the cavity 38a. The stabilizer screw 20 can also, similarly, migrate upward in the elongated slit 30b by moving within the cavity 38a and/or pivot relative to the stabilizer 16 while being retained in the cavity 38a of the opening 30. This particular configuration of the opening 30 and the movement of the stabilizer screw 20 inside the opening 30 can advantageously facilitate a range of motion with the enhanced artificial disk 10 of the present invention that substantially approximates the range of motion of a normal disk.

Figure 6:
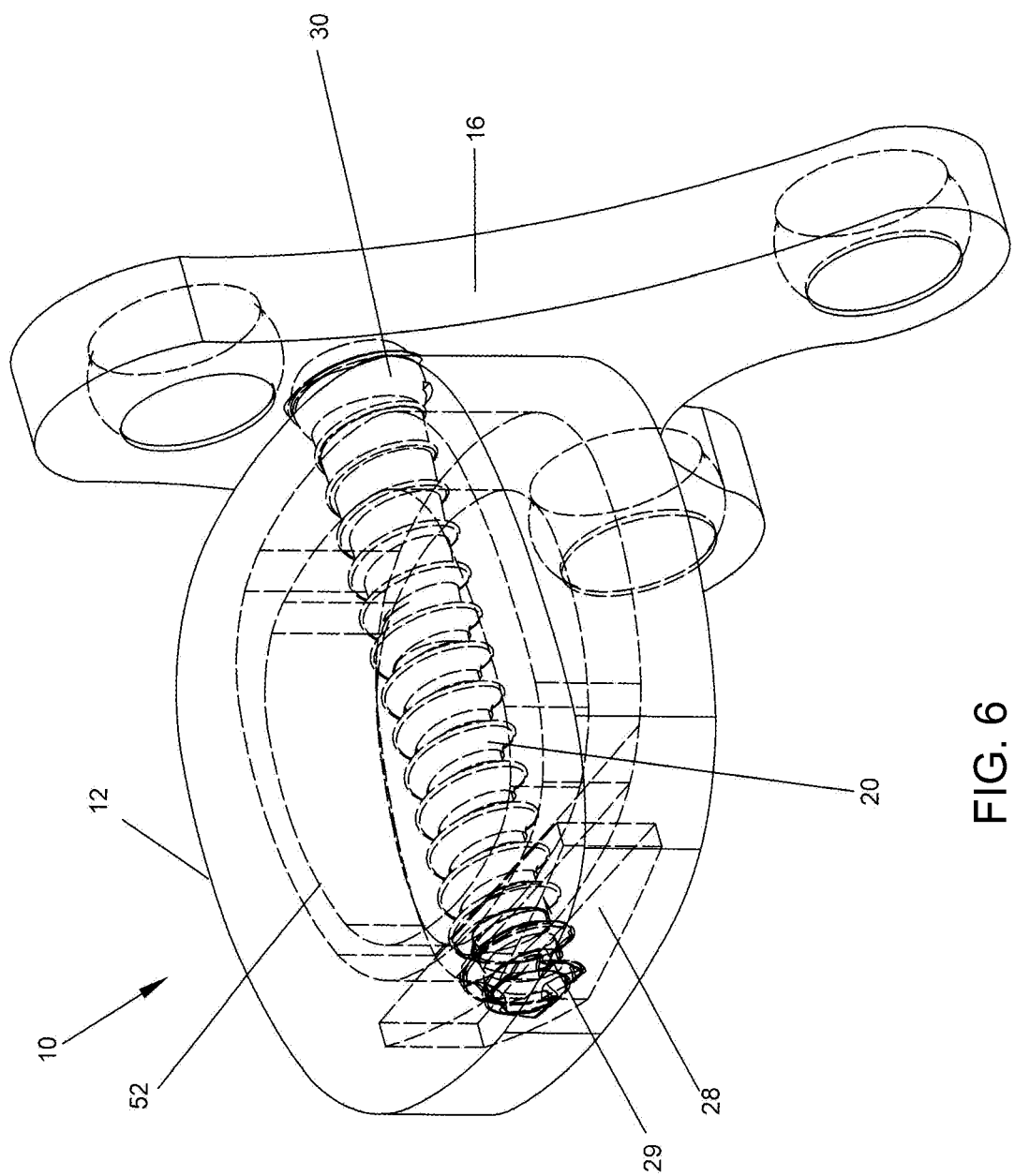
FIG. 6 is a rear view of a pre-assembled enhanced artificial disk in accordance with another embodiment of the invention.

A rear view of another embodiment of a pre-assembled enhanced artificial disk 10 is shown in FIG. 6. The enhanced artificial disk 10 includes a stabilizer 16, disk 12 and stabilizer screw 20. The stabilizer 16 is mounted to the disk 12 through the stabilizer screw 20. The tip of the stabilizer screw 20 is secureably lodged within a groove 29 of an anchor 28. The anchor 28 may be positioned inside the disk 12 at an opposite end to the head of the stabilizer screw 20. The disk 12 may contain a sac 52. The sac 52 may occupy substantially an entire interior hollow space 24 of the disk 12. The sac 52 may be at least partially filled with a hydrogel such as a polyvinyl alcohol (PVA), synthetic silk-elastin copolymers, polymethyl- or polyethylmethacrylate, polyethylene or polyacrylonitrile that absorbs water and increases in volume upon absorption of water, thereby functioning to maintain disk height in a manner similar to the manner in which the healthy disk maintains proper spacing between adjacent vertebrae. To facilitate the absorption of water, the sac 52 may be comprised of a material that is permeable to water and the disk 12 may be provided with a plurality of holes or channels (not shown) or other mechanisms for allowing water to pass through the material comprising the disk 12 and access the permeable sac 52 containing the hydrogel. Materials that may be used to advantage as the sac 52 may include woven polyethylene, woven and non-woven biocompatible synthetic fibers and other materials as known in the art. Since the sac 52 may be contained within the hollow space 24 of disk 12, the strength of the material comprising the sac 52 is not as important as the ability of that material to contain the hydrogel and pass water into and out of the hydrogel in a manner that mimics the absorption of water by the healthy nucleus pulposus. In another embodiment of the invention, the hollow space 24 of disk 12 may be devoid of such a sac 52. In such an embodiment, the hydrogel may be directly injected, as needed, into the hollow space 24 of the disk 12 such that appropriate disk height is maintained with or without the benefit of sac 52.

Figure 7:
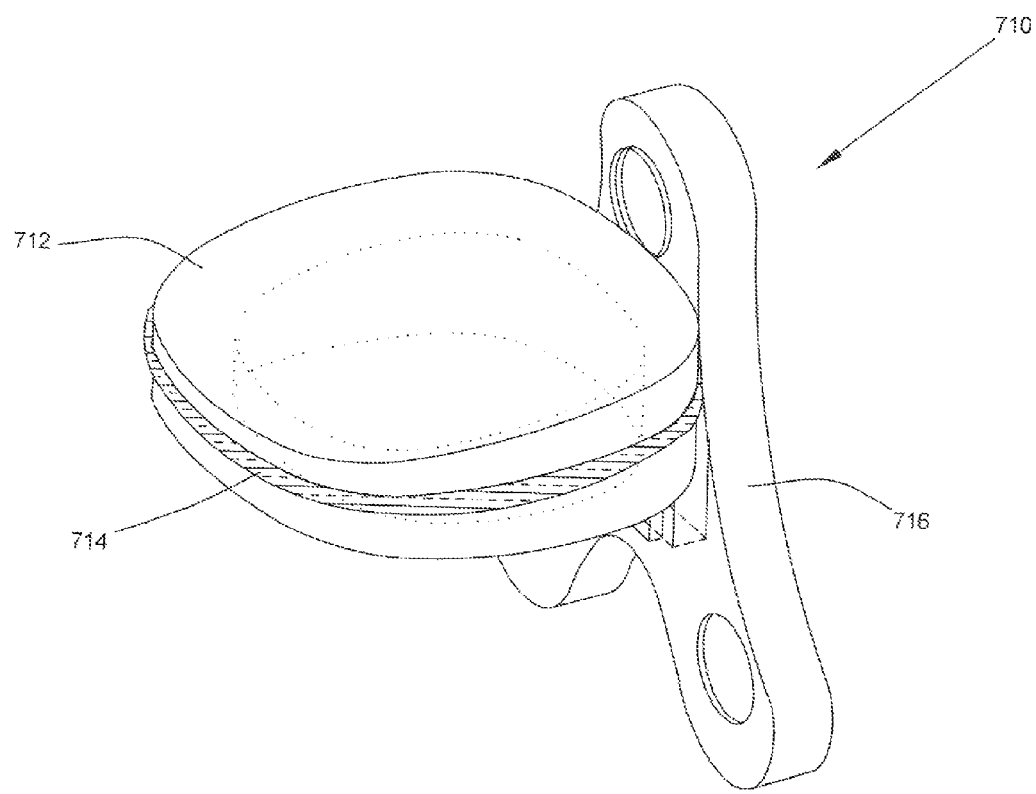
FIG. 7 is a side view of a pre-assembled enhanced artificial disk having a band in accordance with another embodiment of the invention.
Figures 8A, 8B:
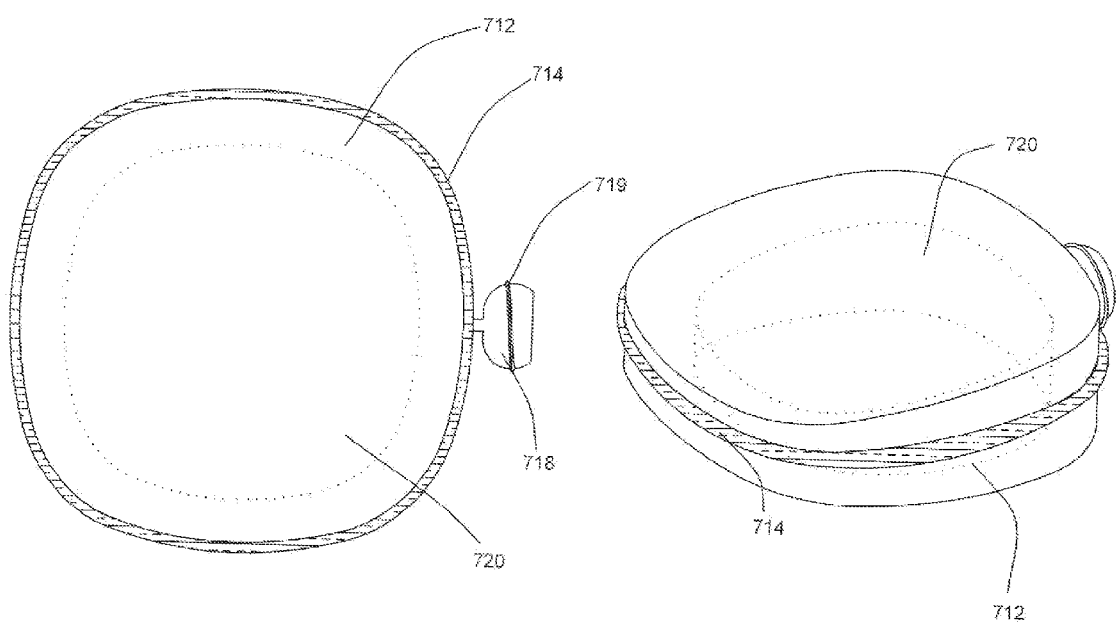
FIGS. 8A-8D illustrate top down, perspective, sectional and side views respectively of the exemplary artificial disk shown in FIG. 7.
Figure 8C:
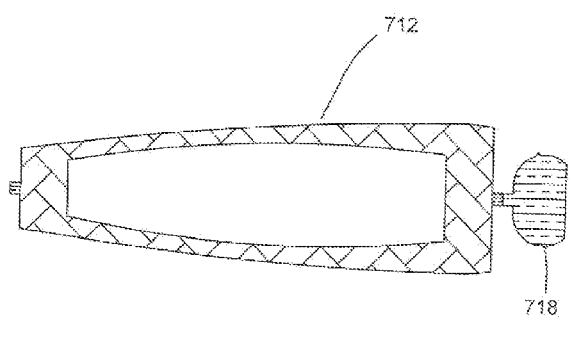
Figure 8D:
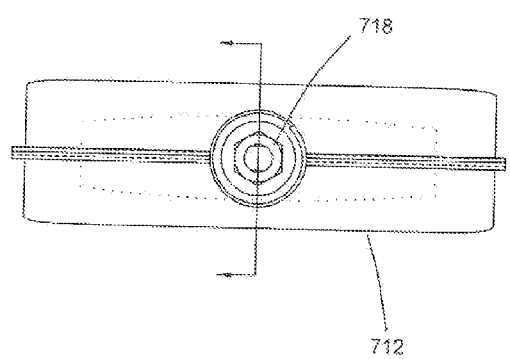

Another embodiment of a pre-assembled enhanced artificial disk 710 is shown in FIG. 7. Referring now to FIG. 7 and FIGS. 8A-8B, the enhanced artificial disk 710 includes a stabilizer 716, disk 712 and a stabilizer band 714. As used herein, the term "band" includes a strip, a strap, a ring or any other suitable flat structure that can extend around the disk 712. The stabilizer band 714 is positioned along a circumference of the disk 712. The stabilizer band 714 may be manufactured from titanium or any suitable biocompatible material.

The stabilizer 716 is mounted to the disk 712 through a knob or protrusion 718 formed on at least one end of the stabilizer band 714. The protrusion 718 may be spherical in shape and, similar to the stabilizer screw described in the previous embodiments, it may be dimensioned and configured to reside within and move along the length of the keyhole shaped opening (as described earlier) of the stabilizer 716. This allows the enhanced artificial disk 710 to approximate the full range of motion of a normal disk. However, unlike the stabilizer screw described earlier, the protrusion 718 does not penetrate into the disk 712 thereby allowing it to maintain the disk 712 full range of properties. The protrusion 718 may have a thread or protuberance 719 on an outer surface thereof. The protuberance 719 may extend only approximately a single turn around the circumference of protrusion 718.

The disk 712 may contain a sac 720. The sac 720 may be at least partially filled with a hydrogel such as a polyvinyl alcohol (PVA), synthetic silk-elastin copolymers, polymethyl- or polyethylmethacrylate, polyethylene or polyacrylonitrile that absorbs water and increases in volume upon absorption of water, thereby functioning to maintain disk height in a manner similar to the manner in which healthy disk maintains proper spacing between adjacent vertebrae. To facilitate the absorption of water, the sac 720 may be comprised of a material that is permeable to water and the disk 712 may be provided with a plurality of holes or channels (not shown) or other mechanisms for allowing water to pass through the material comprising the disk 712 and access the permeable sac 720 containing the hydrogel. Materials that may be used to advantage as the sac 720 may include woven polyethylene, woven and non-woven biocompatible synthetic fibers and other materials as known in the art. The strength of the material comprising the sac 720 is not as important as the ability of that material to contain the hydrogel and pass water into and out of the hydrogel in a manner that mimics the absorption of water by the healthy nucleus pulposus. In another embodiment of the invention, disk 712 may be devoid a sac. In such an embodiment, the hydrogel may be directly injected, as needed, into the disk 712 such that appropriate disk height is maintained without the benefit of sac 720.

FIGS. 4A-4F show an embodiment of the enhanced artificial disk 10 inserted in the intervertebral disk space formed between upper vertebra 34 and lower vertebra 36. When the enhanced artificial disk 10 is inserted into the intervertebral disk space 35, it is subjected to both compression and tension loads as the spine flexes and as the patient moves during his/her normal daily routine. As described earlier, the enhanced artificial disk 10 can include disk 12 and stabilizer 16. The disk 12 is held in position by stabilizer 16. The stabilizer 16 can be affixed to the disk by means of stabilizer screw 20. As shown, the stabilizer 16 can be affixed to the vertebrae by driving nails 32 through the through-holes 17', 17", 17''' of the stabilizer 16. As described earlier, the rear wall (not shown) includes opening 30. The width of the cavity 38a may be larger than the crown 30a and the elongated slit 30b of the opening 30. This may facilitate sideways and lateral movement of the stabilizer screw 20 within the cavity 38a. The stabilizer screw head 21a can also be rotated along the long axis of stabilizer screw 20 inside cavity 38a to accommodate for lateral flexion of the neck to the right or left (clockwise or anticlockwise along its long axis to allow the neck to move/tilt to the right or left) along its long axis inside cavity 38a. The stabilizer 16 with the stabilizer crew 20 can prevent the backward movement of the enhanced artificial disk 10. When compression forces with flexion are applied to the enhanced artificial disk 10, the head 21a of stabilizer screw 20 can move downward inside the cavity 38a. On the other hand, the application of compression forces with extension to the enhanced artificial disk 10 can cause the head 21a of stabilizer screw 20 to move upward inside the cavity 38a. The head 21a can move in multiple directions as needed for the normal ranges of movement of the disk 12 while preventing excessive movements by its inability to get out of the cavity 38a.

FIG. 4A depicts movement of the enhanced artificial disk 10 in a normal spinal position. FIG. 4B shows the movement of the enhanced artificial disk 10 when it is subjected to compression. As can be seen in comparison with FIG. 4A, in FIG. 4B, the height of the disk 12 is shrunk in response to compression forces. FIGS. 4C and 4D depict the movement of the enhanced artificial disk 10 in response to right flexion and left flexion respectively. As can be seen in FIGS. 4C and 4D, the head 21a of stabilizer screw 20 may be rotated in a counterclockwise direction or in a clockwise direction respectively to accommodate right and left flexion. FIGS. 4E and 4F depict the movement of the enhanced artificial disk 10 in response to left and right rotation respectively. As can be seen in FIGS. 4E and 4F, the width of the cavity 38a is larger than the head 21a of the stabilizer screw 20. The head 21a of the stabilizer screw 20 can, therefore, slide or move to the left or to the right inside the cavity 38a to accommodate rotational movements, for example, neck rotation movements.

Figure 4G:
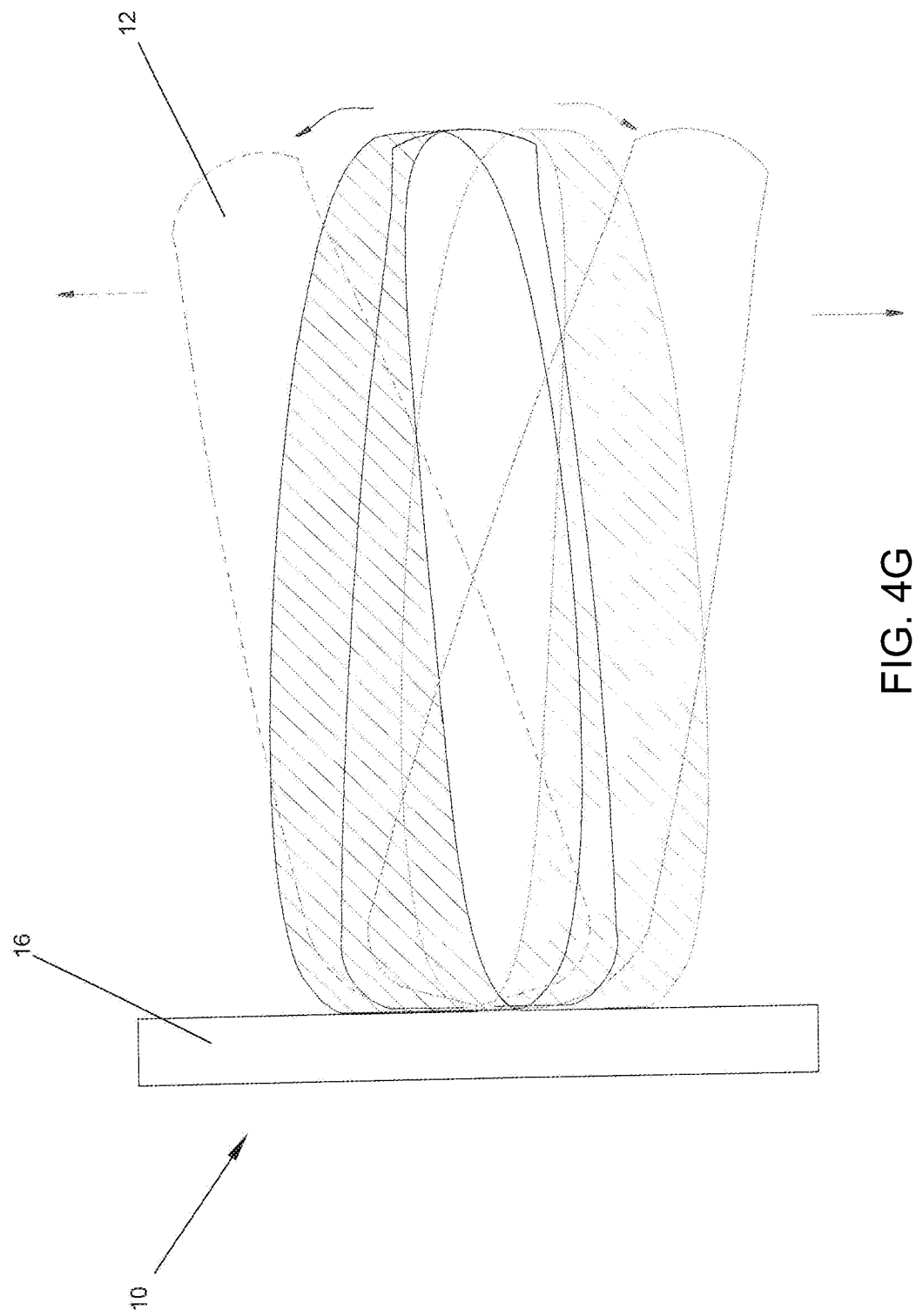
FIGS. 4G-4H depict a range of movement of the enhanced artificial disk in the intervertebral space in accordance with an embodiment of the invention.
Figure 4H:
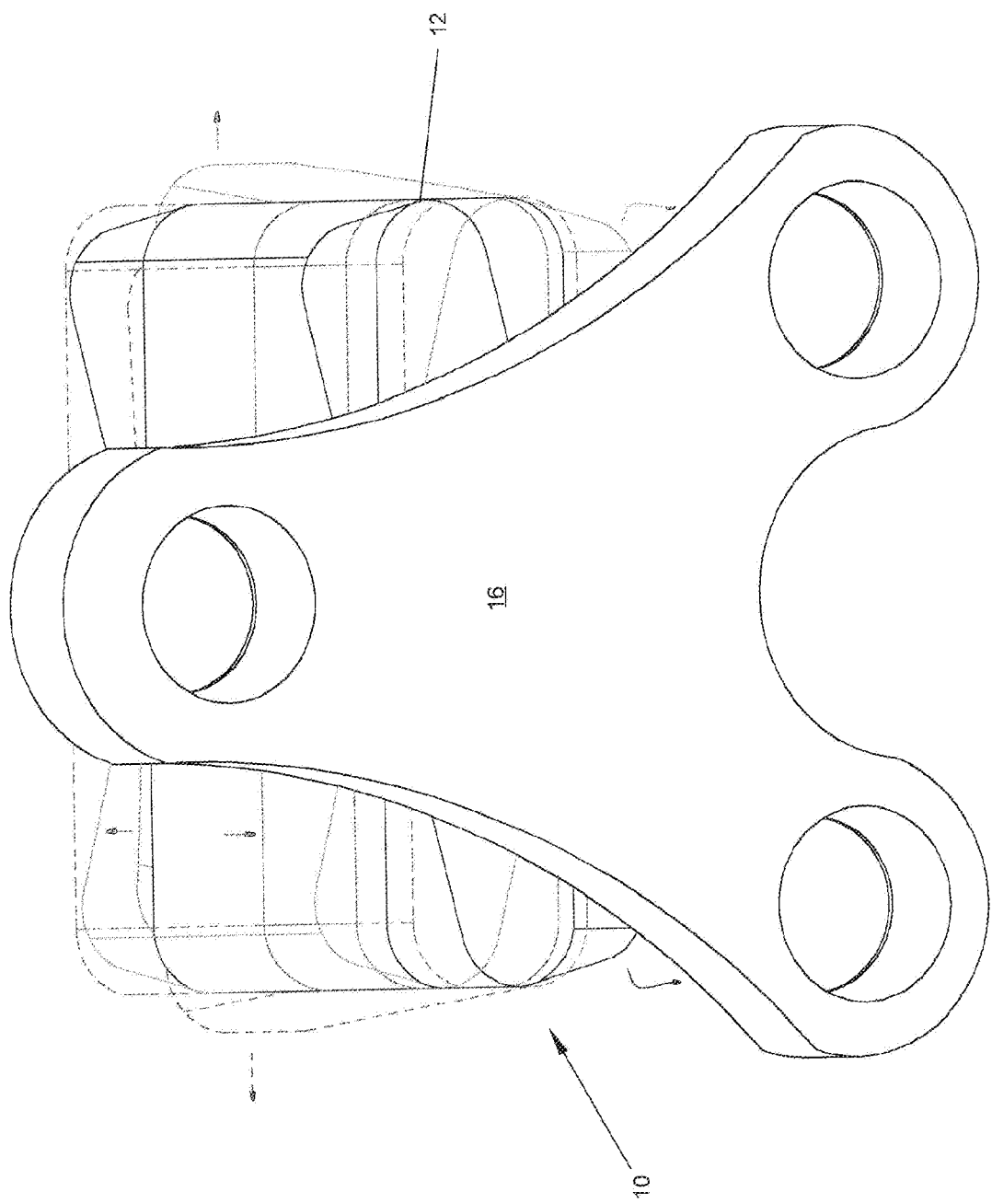

FIGS. 4G and 4H depict the wide range of movement exhibited by the enhanced artificial disk 10 comprising a stabilizer 16 and disk 12. As described earlier, the enhanced artificial disk 10 can respond to flexion, extension, compression, right and left flexion, and right and left rotation in a manner that approximates the movement of a normal disk. The arrows in FIG. 4G show the motion of the enhanced artificial disk 10 in six directions. Curved arrows on the right and left show bending motion towards the right and left respectively (about an imaginary z axis). The up and down arrows show flexion and extension motion respectively (about an imaginary x axis). The right and left arrows shows the right and left rotation of disk respectively (about an imaginary y axis). A side view of the stabilizer 16 is shown in FIG. 4H. The top and bottom directed arrows shows flexion and extension respectively and the bottom and top curved arrows shows right and left bending motion respectively. The range of motions described herein merely for illustration purposes. However, those skilled in the art, will recognize that other ranges of motion are also possible with the specialized coupling of the disk with the stabilizer as disclosed in the various embodiments.

FIG. 4I depicts a neutral side view the enhanced artificial disk 10 comprising a stabilizer 16 and disk 12 in the intervertebral space in accordance with an embodiment of the invention. FIGS. 4J and 4K depict side views showing flexion and extension respectively of an enhanced artificial disk 10 comprising a stabilizer 16 and disk 12 in the intervertebral space in accordance with an embodiment of the invention.

When the respective compression or tension force is relieved, the enhanced artificial disk 10 tends to return to its original shape. When subjected to loads in this manner, the stabilizer 16 acts as a substantially rigid "backbone" and can directs compression loads and relieve tension loads in a manner that mimics normal disk function while at the same time preventing abnormal excessive mobility of the enhanced artificial disk when it is implanted in the intervertebral disk space. Materials that are characterized by this function when formed into the stabilizer 16 include, but are not limited to stainless steel, titanium and titanium alloys, cobalt-chrome (Co—Cr) alloys, cobalt-chromium-molybdenum (Co—Cr—Mo), carbon, silicone, and medical grade (inert) polymeric plastics such as polyethylene, all as known in the art, and any and all other suitable materials as known in the art. In another embodiment, the stabilizer can be made of a material that can substantially deform to add to the mobility of the disk.

A method of implantation of the enhanced artificial disk having a disk and stabilizer in accordance with the one or more embodiments described earlier is now described. The method involves removing the damaged disk (or a portion of the disk) in a patient to be treated. The intervertebral disk space is thoroughly cleaned. The disk space may be distracted by using a special four-prong distractor (not shown) or any other distraction system known in the art. An enhanced artificial disk of appropriate compressibility may be selected based on the strength of the patient's vertebrae. The strength of the vertebrae may be pre-determined by one or more tests known in the art. For example, the strength of the vertebrae may be determined by Bone Mineral Density (BMD) tests, X-rays, CT scans or other such tests. Based on the results of such tests, an enhanced artificial disk having an appropriate compressibility may be selected. The selected disk may have a desired height, width and depth for implantation in the disk space. The enhanced artificial disk may be pre-assembled prior to implantation by connecting the disk with the stabilizer. Alternately, the disk can be connected with the stabilizer in the surgical suite.

The disk may be impacted into the disk space with the stabilizer applied flush to the surface of a pair of upper and lower vertebrae. Pilot holes are drilled in the upper and lower vertebrae using the through-holes in the stabilizer as a template. Nails of appropriate sizes and diameters for the particular patient are selected. The nails may be driven (using a hex key, or Allen wrench, sized to fit the socket opening to the top of the head of the nails) into the upper and lower vertebral bodies at the angle (relative to the plane defined by the apertures of the through-holes in the stabilizer) that is needed to effectively transfer load to the stabilizer. When the nails have been driven into the respective vertebral body far enough that the head of the nails contact the margins of the apertures of the through-holes through which the nails extend, the nails are rotated approximately one rotation to cause the thread on the head of the nails to bite into the margins of the apertures of the through-holes and pull the head through the smaller diameter apertures into central portion of the through-holes. The central portion of the through-holes may have a larger diameter than the apertures of the through-holes. The limited mobility afforded by the nail head inside the through-holes will the complement the controlled range of motion allowed by the screw head inside the cavity of the stabilizer. This range of motion has been described in U.S. Pat. No. 8,317,843, the contents of which are incorporated in its entirety.

Once each of the nail head is positioned in the central portion of the through-holes, additional rotation of the nails (for instance, to tighten the stabilizer against the surfaces of the vertebral bodies) does not change the relative angle or position between the stabilizer and the nails. Stated another way, once the head of nails is positioned in the central portion of the through-holes in the stabilizer and because the head of the nails is of smaller diameter than the diameter of the central portion of the through-holes, the stabilizer and the head of the nails do not change position or angle relative to each other when the nails are rotated relative to the stabilizer because the thread on the head of the nails does not contact the concave side walls of the central portion of the through-holes in the stabilizer (and, as set out above, the nails may be free to rotate or pivot relative to the stabilizer while being retained in the central portion of the through-holes). The head of the nails will not pass through the inner apertures of the holes in the stabilizer plate because the inner appertures are much smaller than the outer apertures. This will prevent the nail head from passing through the stabilizer into the vertebral body. The disk space distractors may now be removed.

At this time, the surgeon has the option to measure the disk pressure from the sac (contained inside the disk) or from the central hollow space of the disk. The pressure can be measured using techniques known in the art. If the disk pressure is lower than an optimal level, the surgeon may be able to inject nucleus-like material that is comparable to the nucleus pulposis of a normal disk into the sac or into the central hollow space of the disk. If the disk pressure is higher than an optimal level, the surgeon can aspirate the material contained in the sac or within the disk. Accordingly, for the first time in the clinical application of disk replacements, the surgeon has the ability to keep the disk pressure at a desired level and maintain an optimal intradiskal height. The disclosed method can also facilitate relatively inexpensive and non-invasive post-surgical maintenance. For example, if the nucleus-like material wears out or the intradiskal pressure is no longer determined to be optimal, the material can be conveniently injected into (or aspirated from) the disk without requiring any invasive or expensive surgical procedure(s).

Once the disk pressure is adjusted, the wound may be closed as usual. The patient should be able to sit up and ambulate soon after the procedure is completed because of the stability imparted to the spine by the implant and method of the present invention.

In another embodiment, a method of intervertebral disk stabilization may include the steps of providing an enhanced artificial disk and implanting the enhanced artificial disk in a patient in the space defined by a first vertebra above and a second vertebra below. The method may include the step of distracting the first and second vertebrae and removing a portion of the intervertebral disk from between the first and second vertebrae. The method may further include pre-selecting the enhanced artificial disk. The pre-selection may of the enhanced artificial disk may be dependent on the enhanced artificial disk having an appropriate compressibility that substantially matches the rigidity of a patient's bones As described earlier, the enhanced artificial disk includes a disk and a stabilizer. The disk includes a substantially firm outer surface and a soft inner surface. The stabilizer is mounted to the disk at a first end to prevent backward movement of the disk. The stabilizer includes a casing having a front wall and a rear wall. The rear wall has a keyhole-shaped opening. The keyhole-shaped opening of the stabilizer has a substantially globular crown and a constricted tail. A cavity is enclosed within the front wall and the rear wall. The front wall and the rear wall have a plurality of through-holes. The method may include receiving a nail in each of the through-holes of the stabilizer. The nails are anchored into the vertebrae above and below.

The method further involves inserting a stabilizer screw in the opening of the stabilizer. The enhanced artificial disk may be allowed a normal range of motion associated with a healthy disk by permitting the head of the stabilizer screw to move within the cavity of the stabilizer. Furthermore, advantageously, any abnormal range of motion of the enhanced artificial disk may be limited by trapping the head of the stabilizer screw within the cavity of the stabilizer. Posterior migration of the disk may be prevented by the stabilizer screw and the disk anchor attachment.

The method may further include controlling the compressibility of the disk by affixing or fastening the disk and the stabilizer to the first and second vertebrae.

The method further involves a controlled shifting of the axis of motion of the vertebrae through the combination of outer firm and inner soft disk segments to approximate the motion of the annulus fibrosis and nucleus pulposis respectively.

Another embodiment includes achieving a substantially large enough annulus like, nucleus like and end plate like combination in a stable construct to approximate the function of a normal disk.

Advantageously, the one or more embodiments of the invention combine the benefit of total disk replacement and nucleoplasty by creating a non ball-and-socket total disk replacement with the desired qualities of nucleoplasty. Furthermore, the self-locking nails that pass through the stabilizer through-holes facilitate simplicity for surgery and complement the normal range of motion facilitated by the disk-stabilizer combination.

Two or more enhanced artificial disks may be stacked at multiple levels using the stabilizer. The stabilizer may be substantially triangle shaped. In the stacked configuration, the tapering top of a first triangle-shaped stabilizer can fit into the inverted U-shaped slot or notch on the base or bottom of a second stabilizer. In a stacked configuration, a top portion of the stabilizer of a first enhanced artificial disk is located within a slot on a bottom portion of the stabilizer of a second enhanced artificial disk. Although the stabilizers are not meant to lock into each other, they can facilitate providing some room between the enhanced artificial disks.

In another embodiment, a method of adjusting intradiskal pressure includes measuring the intradiskal pressure of an enhanced artificial disk. As described earlier, the enhanced artificial disk may include a disk, wherein the disk comprises a comprises a substantially firm outer surface and a soft inner surface; and a stabilizer, wherein the stabilizer is mounted to the disk at a first end to prevent backward movement of the disk. The disk may have a central hollow space. The central hollow space may include a sac. The disk may further include a cushion. The cushion has an allowance (for example, openings or ports) for fluid to permeate into and out of the central hollow space. The stabilizer may include a substantially keyhole-shaped opening. The method may further involve allowing the disk to expand at rest and shrink under compression through an exchange of the fluid between: (A) the central hollow space or the sac, and (B) an external surface through the permeable cushion of the disk.

An optimal threshold value or a range of values for the intradiskal pressure may be pre-determined. If the measured intradiskal pressure does not meet the optimal threshold value or range of values, nucleus-like material may be injected or aspirated into or from the central hollow space of the disk or the sac. The method may also include facilitating continued monitoring of intradiskal pressure by facilitating follow-up measurements of the intradiskal pressure. The intradiskal pressure may be corrected or adjusted if the follow-up measurements reveal a sub-optimal intradiskal pressure.

Although shown in the figures in a configuration that reflects the use of the enhanced artificial disk for replacement of an intervertebral disk in the cervical spine, those skilled in the art will recognize from the following description that, with appropriate changes in size and configuration, the enhanced artificial disk of the present invention may also be utilized to advantage for total disk replacement in the lumbar, thoracic or any other regions of the spine. The lumbar region disk may be replaced from the front as with cervical region. Alternately, the disk can be inserted through other approaches, including, posterior lumbar interbody fusion ("PLIF"), transforaminal lumbar interbody fusion ("TLIF") or extreme lateral interbody fusion ("XLIF") approaches with some modifications while retaining the general principles of the enhanced artificial disk of the invention.

Although described in terms of the preferred embodiments shown in the figures, these embodiments are shown to exemplify the invention, it being recognized by those skilled in the art that certain changes can be made to the specific structure of the embodiments shown and described without departing from the spirit of the present invention. Those skilled in the art will recognize from this description that these embodiments can be utilized in any of several different combinations with equal efficacy. For example, in one embodiment, the stabilizer may be omitted. The disk disclosed herein can be used without the stabilizer in any procedure requiring an artificial disk.

All such modifications, and other modifications which do not depart from the spirit of the present invention, are intended to fall within the scope of the following claims. The terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

The invention claimed is:

1. An enhanced artificial disk comprising:
   a disk, wherein the disk comprises a comprises a substantially firm outer surface and a soft inner surface;
   a stabilizer, wherein the stabilizer is mounted to the disk at a first end to prevent backward movement of the disk; and
   a stabilizer band, wherein the stabilizer band is positioned along a circumference of the disk, wherein the stabilizer band comprises a protrusion for secureably coupling the stabilizer with the disk,
   wherein the stabilizer comprises a casing, wherein the casing comprises a front wall and a rear wall, wherein a cavity is enclosed within the front wall and the rear wall, and wherein the rear wall has a keyhole-shaped opening for receiving the protrusion of the stabilizer band,
   wherein said keyhole-shaped opening includes a substantially globular crown and a constricted tail, and wherein the tail is parallel to a longitudinal axis that extends substantially through the center of the stabilizer;
   wherein, the protrusion is configured to be trapped inside and movable within said cavity of the stabilizer and an overall width of the cavity taken along a direction perpendicular to the longitudinal axis being larger than the substantially globular crown and the constricted tail which facilitates movement of the protrusion between the globular crown and the bottom of the tail within the cavity to allow the enhanced artificial disk to exhibit flexion, extension, compression, left and right lateral flexion and left and right rotation, and also preventing abnormal range of motion of the enhanced artificial disc when it is implanted in space defined by a first vertebra above and a second vertebra below and thus allowing the enhanced artificial disk to approximate full range of motion of a normal disk when it is implanted in the space defined by the first vertebra above and the second vertebra below.

2. The enhanced artificial disk according to claim 1, wherein the disk further comprises a cushion, wherein the cushion encloses a central hollow space, and further wherein the cushion comprises allowance for a fluid to permeate into and out of the central hollow space.

3. The enhanced artificial disk according to claim 2, wherein the central hollow space has a sac therein.

4. The enhanced artificial disk according to claim 3, wherein the sac comprises a material that is permeable to the fluid.

5. The enhanced artificial disk according to claim 1, wherein the protrusion is spherical in shape.

6. The enhanced artificial disk according to claim 1, wherein the longitudinal axis of the stabilizer is positioned at an angle of about 90 degrees to the longitudinal axis of the disk.

7. The enhanced artificial disk according to claim 1, wherein the front wall and the rear wall comprise a plurality of through-holes, wherein each of the through-holes is configured to receive a nail therethrough.

8. The enhanced artificial disk according to claim 7, wherein each of the nails is capable of biting into an outer opening of the through-holes and wherein the nails are configured to thread or anchor into the vertebrae above and below.

9. A method of inter vertebral disk stabilization comprising:
providing an enhanced artificial disk comprising:
a disk, wherein the disk comprises a comprises a substantially firm outer surface and a soft inner surface;
a stabilizer, wherein the stabilizer is mounted to the disk at a first end to prevent backward movement of the disk and a stabilizer band positioned along a circumference of the disk having a protrusion for secureably coupling the stabilizer with the disk, wherein the stabilizer comprises a casing, wherein the casing comprises a front wall and a rear wall, wherein a cavity is enclosed within the front wall and the rear wall, and wherein the rear wall has a keyhole-shaped opening for receiving the protrusion of the stabilizer band, and wherein the keyhole-shaped opening of the stabilizer has a substantially globular crown and a constricted tail and wherein the tail is parallel to a longitudinal axis that extends substantially through the center of the stabilizer;
wherein the front wall and the rear wall comprise a plurality of through-holes;
implanting the enhanced artificial disk into the space defined by a first vertebra above and a second vertebra below, wherein the protrusion is configured to be trapped inside and movable within the cavity, an overall width of the cavity taken along a direction perpendicular to the longitudinal axis being larger than the substantially globular crown and the constricted tail which facilitates movement of the protrusion between the globular crown and the bottom of the tail within the cavity to allow the enhanced artificial disk to exhibit flexion, extension, compression, left and right lateral flexion and left and right rotation, and also preventing abnormal range of motion of the enhanced artificial disc when it is implanted in space defined by the first vertebra above and the second vertebra below; and
receiving a nail in each of the through-holes of the stabilizer, wherein the nails are anchored into the vertebrae above and below.

10. The method according to claim 9, further comprising pre-selecting the enhanced artificial disk, wherein the pre-selected enhanced artificial disk has an appropriate compressibility to substantially match the rigidity of the bones of a patient.

11. The method according to claim 9, further comprising:
inserting a protrusion in the keyhole-shaped opening of the stabilizer;
allowing the enhanced artificial disk to have a normal range of motion associated with a healthy disk by permitting the protrusion to move within the cavity of the stabilizer and head of the nail moving inside the through-holes in the stabilizer; and
limiting an abnormal range of motion of the enhanced artificial disk by trapping the protrusion within the cavity of the stabilizer and the head of the nails in the through-holes of the stabilizer.

12. The method according to claim 9, further comprising:
distracting the first and second vertebrae; and
removing a portion of the inter vertebral disk from between the first and second vertebrae.

13. The method according to claim 9, further comprising controlling the compressibility of the disk by affixing the stabilizer to the first and second vertebrae after lodging the disk in the disk space.

* * * * *